United States Patent
Shihadeh et al.

(10) Patent No.: US 10,849,361 B2
(45) Date of Patent: Dec. 1, 2020

(54) AIRFLOW PUFF TOPOGRAPHY MEASUREMENT DEVICE AND METHOD

(71) Applicant: VIRGINIA COMMONWEALTH UNIVERSITY, Richmond, VA (US)

(72) Inventors: Alan Shihadeh, Beirut (LB); Thomas Eissenberg, Richmond, VA (US)

(73) Assignees: Virginia Commonwealth University, Richmond, VA (US); American University of Beirut, Beirut (LB)

( * ) Notice: Subject to any disclaimer, the term of this patent is extended or adjusted under 35 U.S.C. 154(b) by 482 days.

(21) Appl. No.: 15/749,796

(22) PCT Filed: Jul. 25, 2016

(86) PCT No.: PCT/US2016/043810
§ 371 (c)(1),
(2) Date: Feb. 2, 2018

(87) PCT Pub. No.: WO2017/023589
PCT Pub. Date: Feb. 9, 2017

(65) Prior Publication Data
US 2018/0228215 A1    Aug. 16, 2018

Related U.S. Application Data

(60) Provisional application No. 62/200,350, filed on Aug. 3, 2015.

(51) Int. Cl.
| A24F 47/00 | (2020.01) |
| A24C 5/34 | (2006.01) |
| G01F 1/00 | (2006.01) |
| A24F 40/80 | (2020.01) |
| A24F 21/00 | (2006.01) |
| A61B 5/091 | (2006.01) |

(52) U.S. Cl.
CPC .......... *A24F 47/008* (2013.01); *A24C 5/3418* (2013.01); *A24F 21/00* (2013.01); *A24F 40/80* (2020.01); *A61B 5/091* (2013.01); *G01F 1/00* (2013.01)

(58) Field of Classification Search
CPC .......... A24C 5/34; A24F 40/80; A24F 47/008
See application file for complete search history.

(56) References Cited

U.S. PATENT DOCUMENTS

| 4,400,972 A | 8/1983 | Wiethaup | |
| 2004/0177674 A1 | 9/2004 | Read et al. | |
| 2006/0099554 A1* | 5/2006 | Frost | A24C 5/34 434/236 |
| 2008/0257368 A1 | 10/2008 | Wilson et al. | |
| 2009/0120449 A1* | 5/2009 | Tindall | A24C 5/3406 131/334 |
| 2014/0278258 A1 | 9/2014 | Shafer | |
| 2014/0300480 A1 | 10/2014 | Xiang | |
| 2017/0020198 A1* | 1/2017 | Naqwi | A24F 47/008 |
| 2017/0241906 A1* | 8/2017 | Slurink | A24F 47/008 |

FOREIGN PATENT DOCUMENTS

WO    2015/087045 A1    6/2015

* cited by examiner

*Primary Examiner* — Eric Yaary
(74) *Attorney, Agent, or Firm* — W&C IP

(57) ABSTRACT

Provided herein is a device for measuring puff topography generated by a human user of a smoking device and methods for using the same. The device may be used for research on puffing behavior of tobacco product users in both clinical and non-clinical settings.

6 Claims, 3 Drawing Sheets

AIRFLOW PUFF TOPOGRAPHY MEASUREMENT DEVICE AND METHOD

FIELD OF THE INVENTION

The invention is generally related a device for measuring puff topography generated by a user of a smoking device and methods of using the same. The device and methods of the invention may be used for research on puffing behavior of tobacco product users in both clinical and non-clinical settings.

BACKGROUND OF THE INVENTION

Existing puff topography measurement devices measure the aerosol flow exiting a smoking device and require a special mouthpiece to be fitted on the outlet of the smoked device. This mouthpiece alters the feel of the device and can alter the chemical constituents of the aerosol drawn by the user (e.g. nicotine vapors can condense on the mouthpiece's inner surfaces). In addition, because these devices are in direct contact with the aerosol exiting a tobacco product, they must rely on indirect flow measurement to protect sensitive measurement electronics from fouling.

In order to address this limitation, these devices monitor the pressure differential induced across an orifice as the aerosol flows through it: the greater the flow rate, the greater the pressure differential. However, this measurement approach suffers from a limited dynamic measurement range and its accuracy is influenced by variations in pressure and temperature. In addition, because the pressure transducers involved in these devices are inherently "noisy", data acquired using this approach must always be cleaned to eliminate false signals, and doing so can introduce biases. Finally, devices based on differential pressure measurement involve a tradeoff between flow rate sensitivity and draw resistance: the more accurate the device, the harder it is for the user to puff through it.

U.S. Pat. No. 6,814,083 B2 and U.S. Pat. No. 7,164,993 describe the CReSS device that is used as a means for acquiring smoking topographical information. The device is designed for measuring a number of parameters associated with tobacco cigarette behavior. The measurement of puff topography of e-cigarettes is not contemplated. Further, the device measures outflow, rather than inflow of the smoking device, and does so using a mouthpiece and pressure transducer. Methods of using the CReSS device are also found in Perkins et al., The Reliability of Puff Topography and Subjective Responses During Ad lib Smoking of a Single Cigarette. *Nicotine & Tobacco Research*, Vol 14, No. 4 (April 2012) 490-494. The CReSS device and a similar device which, like CReSS, relies on a pressure transducer and mouthpiece to measure aerosol outflow have been used to measure puff topography in electronic cigarette users (Goniewicz et al., Nicotine levels in electronic cigarettes, *Nicotine & Tobacco Research*, 2013, Vol 15, No 1, 158-166; Spindle et al., Preliminary results of an examination of electronic cigarette user puff topography: the effect of a mouthpiece-based topography measurement device on plasma nicotine and subjective effects, *Nicotine & Tobacco Research*, 2015, Vol 17, No 2, 2015, 142-149).

Talih et al. (Effects of User Puff Topography, Device Voltage, and Liquid Nicotine Concentration on Electronic Cigarette Nicotine Yield: Measurements and Model Predictions, *Nicotine & Tobacco Research*, 2015, 150-157) describes the use of a "custom-designed digital puff production machine" to generate aerosol from an e-cigarette. The machine is a model of human puff behavior, however, the device cannot be used to analyze a human user smoking/puffing an e-cigarette. Shihadeh et al. (A portable, low-resistance puff topography instrument for pulsating, high flow smoking devices. *Behavior Research Instruments, Methods, Computers*, Vol 37, 2005, 186-191) describes an apparatus for measuring puff topography of water-pipe smokers. The apparatus could be used to measure topography for cigarettes, pipes and marijuana cigarettes, but there is no description of use with electronic smoking devices. This device also uses a mouthpiece and pressure transducer to measure puff topography.

Devices for measuring puff topography generated by a human smoker that overcome the above-described limitations are lacking in the prior art. Further, the impending likelihood of FDA regulations on e-cigarettes will increase the need for appropriate data-collection tools.

SUMMARY OF THE INVENTION

An aspect of the invention relates to a device for measuring puff topography generated by a user of a smoking device, such as an electronic cigarette (e-cigarette). The device may be used for research on puffing behavior of tobacco product users in both clinical settings, such as academic, industry, or regulatory research laboratories, and in non-clinical settings, e.g. for personal use by the subject. The acquisition of data regarding puff behavior is a critical variable linking e-cigarette characteristics with exposure to nicotine and other toxicants.

Thus, an embodiment of the invention provides a puff topography apparatus for providing puff topographical information, comprising: a holder comprising a flow sleeve wherein an electronic smoking device is received, wherein said holder has a tubular structure of a size suitable for said electronic smoking device, and wherein each end of said electronic smoking device extends beyond said holder; a means for applying a seal around said electronic smoking device at each end of said tubular structure; an air inlet to permit air intake into said tubular structure; a flow sensor for measurement of air flow into said tubular structure; a means for data acquisition; and a power supply.

In some embodiments, the means for data acquisition is embedded on an electronic board containing a microprocessor and replaceable battery. In some embodiments, the electronic board, flow sensor, and holder are mounted in a single enclosure. In other embodiments, the means for data acquisition and flow sensor are mounted in an externally powered enclosure which is attached to the holder via flexible tubing.

Another aspect of the invention provides a method for measuring puff topography of a subject smoking an electronic smoking device, comprising the steps of: placing said electronic smoking device within a holder comprising a flow sleeve operably connected to an air inlet and a flow sensor, wherein each end of said electronic smoking device extends beyond said holder; sealing the ends of said flow sleeve around said electronic smoking device, wherein airflow is channeled through a single inlet; providing said electronic smoking device arranged in said holder to said subject for smoking; measuring flow rate of air entering said air inlet and passing through said electronic smoking device for each puff performed during said smoking step; and acquiring and analyzing flow rate associated with at least one puff performed in said smoking step. In some embodiments, at least one of the parameters selected from the group consisting of puff volume, interpuff interval, and puff duration is measured in said acquiring and analyzing step.

DETAILED DESCRIPTION

Figure 1:
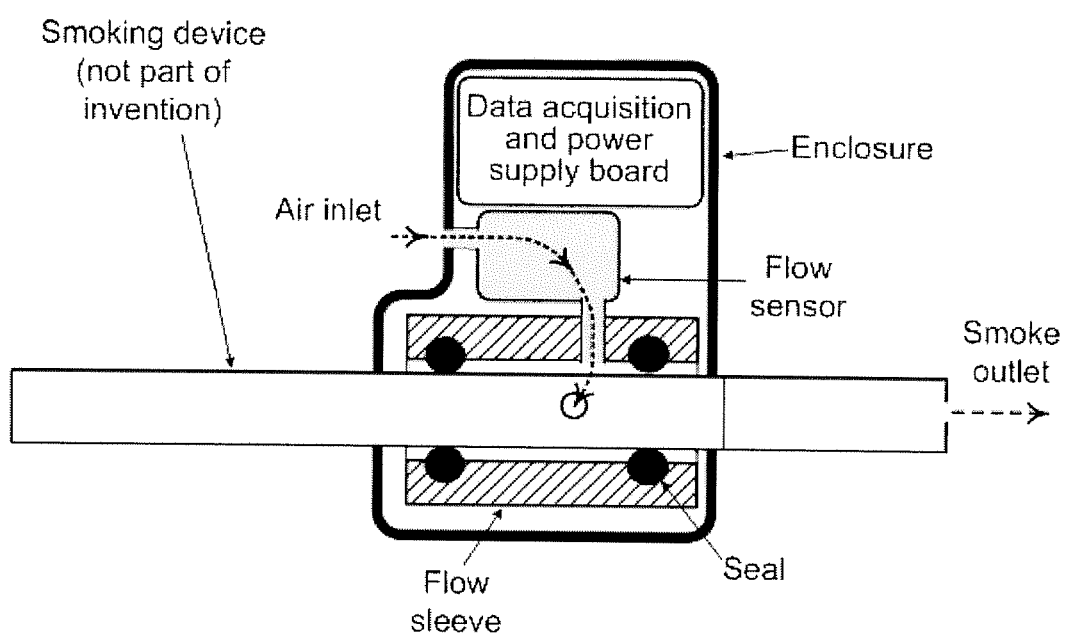
FIG. 1. Air flow puff topography apparatus based on measurement of air flow into a smoking device such as an electronic cigarette. Configuration shown for a self-contained portable unit.

The device of the invention measures air entering the tobacco product instead of the aerosol exiting it. Thus, it does not necessitate the use of a pressure-based measurement principle and does not require installation of a mouthpiece. Because the novel method measures air inlet flow rather than aerosol exit flow, a mass flow sensor (e.g. a hot wire mass flow sensor) can be used to directly measure the flow rate of air without risk of fouling by the aerosol. Compared to pressure differential devices, mass flow sensors are highly stable and accurate, and do not involve an inherent tradeoff between flow rate sensitivity and draw resistance. Using commercially available components, the device allows for a wide dynamic range (e.g. 1 to 300 ml/s measurement range with 2% accuracy of reading). In addition, signals acquired using this principle do not require clean up. In addition, because the device does not require a mouthpiece, the device does not modify the chemical composition or physical properties of the aerosol exiting the tobacco product. The apparatus of the invention is useful for research on puffing behavior of tobacco users in both clinical and natural settings. The device may be used with smoking devices which utilize air inlet passages that can be channeled using a flow sleeve.

The apparatus of the invention can measure smoking topographical information including, but not limited to: puff volume, interpuff interval (IPI), puff duration, peak puff flow rate during puff, and average flow during puff. Puff volume is the amount of smoke drawn by the subject in one puff. Inter-puff interval is the length of time between the start of one puff and the end of the immediately preceding puff of the smoking material by the subject. Puff duration is the time between the start and end of a puff by a subject. Peak puff flow rate is the highest flow rate of smoke into the subject during a puff. Time of peak puff flow rate is the point in time when the highest flow rate of smoke into the subject during a puff is recorded. Average puff flow rate is the average flow rate of smoke into the subject during a puff.

In some embodiments, the apparatus of the invention is portable. By "portable", it is meant that the apparatus, whether by its individual parts or not, is carryable by hand. For example, the apparatus may be carried by the subject and used to record the smoking behavior of the subject in the field. Such measurements may be recorded over a period of time (e.g. for a month or longer) and the data subsequently downloaded to a computer. In other embodiments, the data may be submitted wirelessly to a computer and presented in real-time on a computer or other device, such as a smartphone or smartwatch.

The smoking device used with the invention has a location where a flow sleeve can be installed and where all the air flow entering the smoking device can be channeled through the mass flow sensor (e.g. e-cigarettes). This arrangement would not work on a combustible cigarette since the cigarette rod burns down during use.

The device of the invention allows for the accurate and convenient determination of puff behavior by monitoring the air flow entering a tobacco product during puffing. An exemplary embodiment of the apparatus of the invention is shown in FIG. 1. Methods of using the apparatus involve measuring the rate of air flow drawn into the tobacco product during each puff. In particular, the apparatus allows for the measurement, acquisition, and digital storage of the flow rate of air drawn into a tobacco product, such as an electronic cigarette.

The apparatus shown in FIG. 1 comprises a sealed sleeve fitting that slides over the air inlet holes of the tobacco product, channeling all inlet air through an opening connected to a mass flow sensor. In some embodiments, the sleeve will be sealed at the ends using groove-mounted o-rings or other flexible materials that can accommodate a range of tobacco product dimensions and shapes.

The flow sensor may be a calorimetric device or laminar flow element or other device of low flow resistance.

Figure 2:
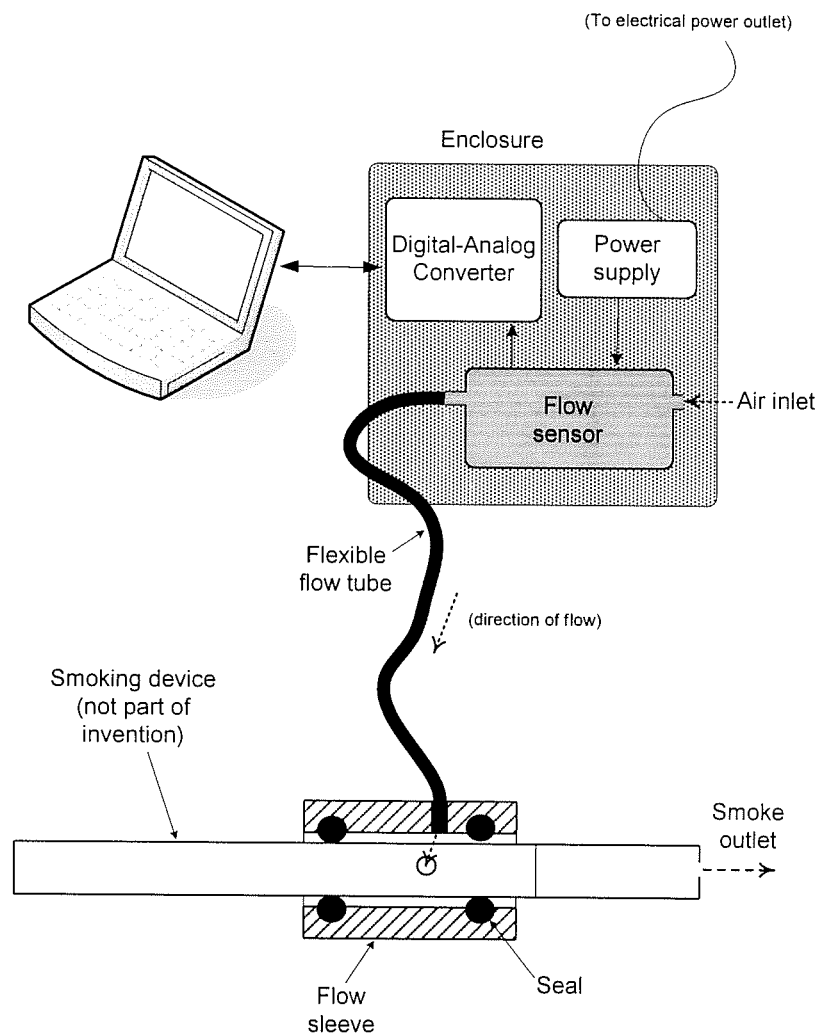
FIG. 2. Air flow puff topography apparatus based on measurement of air flow into a smoking device such as an electronic cigarette. Configuration shown for a desktop unit in which the flow holder is attached via flexible tube to an externally powered device.

As shown in FIGS. 1 and 2, an electronic board containing a data acquisition device (daq) and battery records and stores the instantaneous signal of the mass flow sensor and provides the needed electrical power. The data acquisition means can include an analog to digital converter, memory card, and microprocessor, while data processing means can include a computer, with a processor, the computer being loaded with a suitable program to read data from the device of the invention. The data processing means can carry out the necessary calculations to determine the smoking topographical information.

The system may be configured for portable or clinical applications. When configured for portable applications, the daq can be embedded on an electronic board containing a microprocessor and replaceable battery. The board, mass flow meter, and sleeve can be mounted in a single compact enclosure. When configured for clinical applications, the daq and flowmeter can be installed in an externally powered enclosure which is attached to the sleeve via flexible tubing. The sleeve is connected by a flexible tube to the mass flow meter, which, in turn, is connected by electrical wires leading to a computer-powered daq. Both configurations use software which produces measures of puff topography (including, but not limited to, puff volume, interpuff interval, and puff duration) from the recorded flow rate signal.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range.

Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

puffs drawn (puffy), bout duration (total time elapsed from start of first puff to end of final puff), puffing time (cumulative duration of all puffs executed during a bout), average and standard deviation of puff duration (Avg. Duration, Duration SD), average flow rate during puffing (Avg. Flow), average and standard deviation of interpuff interval (time between puffs; IPI, IPI SD), average and standard deviation of puff volume (Avg. Volume, Volume SD), cumulative volume drawn during a puff (Total Volume), and maximum puff volume drawn (Max Volume). The data shown in Table 1 are within the ranges previously reported by Spindle et al. in which 13 experienced electronic cigarette users executed 5 minute puffing bouts in a clinical study in which a mouthpiece-pressure transducer based topography device was attached to the electronic cigarettes. E.g. Spindle et al. reported average±standard deviation puff duration of 4.16±1.06 s, puff volume of 101±50 ml, and flow rate of 24.2±10.7 ml/s. These numbers are not statistically significantly different than the means of the data reported in Table 1: puff duration 3.95±1.14 s, puff volume 67.4±37.0, flow rate 16.7±7.5 ml/s.

TABLE 1

| ID | Group | Bout | Puff # | Bout Duration (s) | Puffing Time (s) | Avg Duration (s) | Duration SD | Avg. Flow (ml/s) | Avg. IPI (s) | IPI SD | Avg. Volume (ml) | Volume SD | Total Volume (ml) | Max Volume (ml) |
|----|-------|------|--------|-------------------|------------------|------------------|-------------|------------------|--------------|--------|------------------|-----------|-------------------|-----------------|
| 01 | Naïve | 1 | 10 | 311 | 19 | 2.91 | 0.34 | 14.83 | 30.67 | 0.75 | 43.17 | 3.9 | 431.68 | 49.65 |
|    |       | 2 | 7  | 312 | 29 | 4.2  | 1.11 | 12.9  | 44.6  | 34.7 | 54.16 | 8.16 | 379.15 | 67.41 |
|    |       | 3 | 9  | 308 | 28 | 3.11 | 1.06 | 12.88 | 32.25 | 12.06 | 40.08 | 14.16 | 360.69 | 57.13 |
| 02 | Experienced | 1 | 11 | 329 | 43 | 3.87 | 0.94 | 9.73  | 28.22 | 9.51 | 37.7  | 11.99 | 414.66 | 49 |
|    |       | 2 | 2  | 305 | 13 | 6.35 | 0.07 | 12.41 | 216   | N/A  | 78.77 | 21.97 | 157.55 | 94.31 |
|    |       | 3 | 3  | 309 | 19 | 6.2  | 0.1  | 13.75 | 104.15 | 10.11 | 85.27 | 4.2 | 255.82 | 87.82 |
| 03 | Naïve | 1 | 10 | 317 | 46 | 4.56 | 0.68 | 32.89 | 29.84 | 1.84 | 149.97 | 33.69 | 1499.72 | 199.16 |
|    |       | 2 | 11 | 312 | 42 | 3.84 | 1.01 | 28.43 | 23.29 | 7.26 | 109.08 | 34.02 | 1199.93 | 144.9 |
|    |       | 3 | 13 | 312 | 58 | 4.47 | 1.73 | 28.21 | 20.11 | 8.33 | 126.08 | 43.25 | 1639.04 | 215.97 |
| 04 | Naïve | 1 | 12 | 310 | 38 | 3.17 | 0.8  | 19.09 | 24.64 | 11.71 | 60.45 | 17.52 | 725.4 | 87.14 |
|    |       | 2 | 11 | 315 | 42 | 3.79 | 0.5  | 17.35 | 25.22 | 13.11 | 65.78 | 10.41 | 723.6 | 82.91 |
|    |       | 3 | 12 | 314 | 40 | 3.32 | 0.44 | 17.9  | 23.94 | 10.03 | 59.51 | 10.5 | 714.06 | 82.01 |
| 05 | Experienced | 1 | 10 | 322 | 44 | 4.38 | 1.05 | 12.97 | 30.59 | 0.76 | 56.79 | 13.27 | 567.92 | 72.69 |
|    |       | 2 | 17 | 302 | 46 | 2.68 | 1.52 | 6.95  | 13.86 | 13.35 | 18.6 | 12.07 | 316.16 | 37.02 |
|    |       | 3 | 12 | 314 | 30 | 2.48 | 0.97 | 10.51 | 21.35 | 25.56 | 26.02 | 11.64 | 312.24 | 38.78 |

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Embodiments of the invention are further illustrated by the foregoing Examples, which should not be interpreted as limiting the invention in any way.

Example 1. Airflow Puff Topography Analysis

Figure 3:
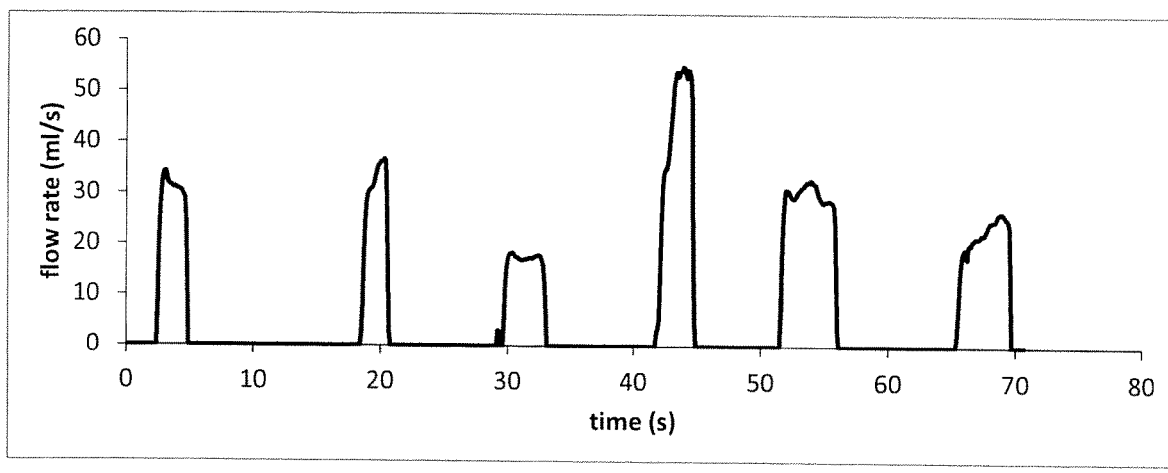
FIG. 3. A sample time trace of flow rate in which six puffs were executed by the user.

A group of 5 individuals was recruited in a clinical study of electronic cigarette use. These individuals included 3 persons who had not previously used electronic cigarettes ("naïve", Table 1) and two experienced electronic cigarette users. Each individual was asked to use an electronic cigarette for three 5-minute bouts while the device of the invention in its embodiment shown in FIG. 2 was attached. The measured variables, shown in Table 1, were number of Example 2. Electronic Cigarette Airflow Recording The device of the invention was used to record puff flow rates drawn by an electronic cigarette user in a clinical laboratory study. Such measurement can be used to program a smoking machine to model human puffing. FIG. 3 shows a sample time trace of flow rate, in which six puffs were executed by the user.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. A puff topography apparatus for providing puff topographical information, comprising:
    a holder comprising a flow sleeve wherein an electronic smoking device is received, wherein the holder has a tubular structure of a size suitable for said electronic smoking device and wherein each end of said electronic smoking device extends beyond said holder;
a means for applying a seal around said electronic smoking device at each end of said tubular structure;
an air inlet to permit air intake into said tubular structure;
a flow sensor for measurement of air flow into said tubular structure;
a means for data acquisition; and
a power supply.

2. The puff topography apparatus of claim 1, wherein the means for data acquisition is embedded on an electronic board containing a microprocessor and replaceable battery.

3. The puff topography apparatus of claim 2, wherein the electronic board, flow sensor, and holder are mounted in a single enclosure.

4. The puff topography apparatus of claim 1, wherein the means for data acquisition and flow sensor are mounted in an externally powered enclosure which is attached to the holder via flexible tubing.

5. A method for measuring puff topography of a subject smoking an electronic smoking device, comprising the steps of:

placing said electronic smoking device within a holder comprising a flow sleeve operably connected to an air inlet and a flow sensor, wherein each end of said electronic smoking device extends beyond said holder;

sealing the ends of said flow sleeve around said electronic smoking device, wherein airflow is channeled through a single inlet;

providing said electronic smoking device arranged in said holder to said subject for smoking;

measuring flow rate of air entering said air inlet and passing through said electronic smoking device for each puff performed during said smoking step; and acquiring and analyzing flow rate associated with at least one puff performed in said smoking step.

6. The method of claim 5, wherein at least one of the parameters selected from the group consisting of puff volume, interpuff interval, and puff duration is measured in said acquiring and analyzing step.

\* \* \* \* \*